United States Patent
Binstead et al.

(10) Patent No.: US 7,144,488 B2
(45) Date of Patent: Dec. 5, 2006

(54) ELECTRODE, ELECTROCHEMICAL CELL, AND METHOD FOR ANALYSIS OF ELECTROPLATING BATHS

(75) Inventors: Robert A. Binstead, Marlborough, MA (US); Osnat Younes-Metzler, Copenhagen Ø (DK); David A. Valeri, Leominster, MA (US); Robert D. Mikkola, Grafton, MA (US)

(73) Assignee: Shipley Company, L.L.C., Marlborough, MA (US)

(*) Notice: Subject to any disclaimer, the term of this patent is extended or adjusted under 35 U.S.C. 154(b) by 328 days.

(21) Appl. No.: 10/455,558

(22) Filed: Jun. 5, 2003

(65) Prior Publication Data

US 2004/0089538 A1    May 13, 2004

Related U.S. Application Data

(60) Provisional application No. 60/386,135, filed on Jun. 5, 2002.

(51) Int. Cl.
   - *G01N 27/26* (2006.01)
   - *G01N 27/30* (2006.01)
   - *G01N 27/403* (2006.01)

(52) U.S. Cl. .......... 205/81; 204/280; 204/412; 204/434; 205/775; 205/787

(58) Field of Classification Search ........ 204/280, 204/434; 205/81, 775, 787
See application file for complete search history.

(56) References Cited

U.S. PATENT DOCUMENTS

| | | | |
|---|---|---|---|
| 4,012,308 A * | 3/1977 | Jerrold-Jones et al. ...... 204/420 |
| 4,132,605 A | 1/1979 | Tench et al. | |
| 4,378,280 A | 3/1983 | Dufau | |
| 4,897,165 A | 1/1990 | Bernards et al. | |
| 4,917,774 A | 4/1990 | Fisher | |
| 4,932,518 A | 6/1990 | Bernards et al. | |
| 5,004,672 A | 4/1991 | D'Ottavio et al. | |
| 5,062,930 A | 11/1991 | Dillon et al. | |
| 5,202,222 A | 4/1993 | Harris et al. | |
| 5,223,118 A | 6/1993 | Sonnenberg et al. | |
| 5,384,229 A | 1/1995 | Pai et al. | |
| 5,635,043 A * | 6/1997 | Tur yan et al. ............. 204/412 |
| 5,980,712 A * | 11/1999 | Tauber et al. ............... 204/435 |
| 6,174,417 B1 | 1/2001 | Henington et al. | |
| 6,241,860 B1 | 6/2001 | Huang et al. | |
| 6,251,234 B1 | 6/2001 | Henington et al. | |
| 6,261,425 B1 | 7/2001 | Huang et al. | |
| 6,653,842 B1 * | 11/2003 | Mosley et al. .............. 324/446 |
| 2002/0043467 A1 | 4/2002 | Morrissey et al. | |

OTHER PUBLICATIONS

Bott, A. W. Current Separations. 1995, 14, pp. 64-68.*
Elmer T. H. "Porous and Reconstructed Glasses" Engineered Materials Handbook, vol. 4, 1992, pp. 427-432.*
McCarron, T. "Silver/Silver Chloride Electrode" http://www.tannerm.com/ag_ref.htm Copyright 1998.*
Bard, A. J. and Faulker, L. R. Electrochemcial Methods. John Wiley and Sons, New York: 1980. pp. 16-17.*

* cited by examiner

*Primary Examiner*—Roy King
*Assistant Examiner*—William T. Leader
(74) *Attorney, Agent, or Firm*—S. Matthew Cairns

(57) ABSTRACT

A counter electrode for use in an electrochemical cell suitable for analysis of an electroplating composition, the counter electrode comprising a conductor; a sheath disposed about the conductor; an electrolyte disposed within the sheath; and an optionally porous element on the sheath, the porous element providing signal communication between the electrolyte and an analyte.

10 Claims, 1 Drawing Sheet

ELECTRODE, ELECTROCHEMICAL CELL, AND METHOD FOR ANALYSIS OF ELECTROPLATING BATHS

This Application claims the benefit of U.S. Provisional Application Ser. No. 60/386,135, filed on Jun. 5, 2002.

BACKGROUND

The present invention relates to electroplating, and more particularly to an improved anode for analyzing organic additives in an electroplating bath.

Electroplating is a complex process involving an electroplating bath with multiple constituents. Acid copper electroplating baths, for example, contain constituents such as a source of copper, a source of acid, optionally a low level of chloride, and organic additives such as accelerators, suppressors, and levelers. It is important that the concentration of these constituents be kept within close tolerances to obtain a high-quality deposit. In some cases, the levels of additives are adjusted based on "rules of thumb" developed over time. In other cases, analysis of individual constituents can be made regularly and additions made as required, for example pH measurements made for acid content. However, organic constituents such as brighteners, leveling agents, suppressors, and the like, together with various impurities that can affect the quality of a deposit, are more difficult to individually analyze on an economic and/or timely basis, especially when the operating concentrations of these materials are low (e.g., less than 1 part per million by weight).

U.S. Pat. No. 4,134,605 to Tench is directed to a method of evaluating concentrations of components typically found in electroplating baths. The method is based on an electrochemical cell with a working electrode that functions as the cathode during copper deposition, a counter electrode that functions as the anode during deposition, and a reference electrode that is immersed in the analyte solution from an electroplating bath. Typically, the working electrode is inert in the bath, and may be a rotating disk to maintain relative motion between the bath and the electrode itself in order to maintain a constant flux of bath components at the working electrode. A voltammetric cycle "sweep" potential is applied between the working electrode and the counter electrode, wherein the sweep is controlled by a function generator. The counter electrode is coupled in series with the function generator to form a coulometer used to measure the current utilized during various portions of the voltammetric cycle.

A calibration curve is produced by sweeping the working electrode through the voltammetric cycle in a series of electroplating baths of known analyte concentration. A portion of the current-use profile generated by each of these bath analyses is then correlated to the concentration of the analyte of interest. Analysis of a bath with an unknown concentration of this analyte can then be determined by comparing a measured, current-use profile to that of the calibration curve. Accordingly, the success of determining an analyte concentration is directly tied to the precision with which the analysis can be produced.

However, during continuous use of an electroplating bath, and following successive analyses, contaminants often accumulate on the electrodes, which has a detrimental effect on the analysis. Attempts to decrease or prevent contamination on the working electrode include sequentially pulsing the working electrode between appropriate metal plating, metal stripping, and cleaning operations, and by applying an equilibrium potential between pulses to maintain a clean and reproducible surface. In particular, U.S. Pat. No. 4,917,774 to Fisher is directed to preventing buildup on the working electrode by using a pulsed sweep without applying a potential following each completed cycle, or by applying a potential equal to or approximately equal to the open circuit potential of the working electrode in the bath following the cycle of metal plating, metal stripping, and cleaning.

However, such methods are only a partial solution, as they do not address accumulation of organic by-products and other bath materials on the counter electrode. This phenomenon manifests itself in both inaccurate (10–30% error) and irreproducible analyses for various analytes. This is especially true when the component concentration must be determined in a solution containing a relatively large excesses of other bath components (e.g., determining the concentration of a leveler in the presence of accelerators and suppressors). Accordingly, a counter electrode capable of sustained use in an electroplating bath would be beneficial, and in particular, a counter electrode that resists becoming coated or otherwise obstructed by organic materials present in the electroplating bath.

STATEMENT OF INVENTION

The present invention provides a counter electrode for use in all electrochemical cell to an analyze an electroplating composition, the counter electrode comprising a conductor; a sheath disposed about the conductor; an electrolyte disposed within the sheath; and a porous element on the sheath the porous element providing signal communication between the electrolyte and an analyte.

In another aspect, an electrochemical cell for analyzing an analyte solution from an electroplating composition comprises a working electrode; a reference electrode; and a counter electrode in operable communication with the working and reference electrodes, wherein the counter electrode is in signal communication with the analyte solution, and wherein the counter electrode comprises a conductor; a sheath disposed about the conductor; an electrolyte disposed within the sheath; and a porous element on the sheath, the porous element providing signal communication between the electrolyte and an analyte.

The present invention further provides a method of determining an analyte concentration in an electroplating composition, comprising contacting an electrochemical cell having a working electrode, a reference electrode, and a counter electrode, wherein the counter electrode is in signal communication with an analyte solution from the electroplating composition; applying a voltammetric sweep cycle to the working electrode; measuring an integrated current (charge) utilized during a portion of the voltammetric sweep cycle representative of the analyte concentration; and comparing measured integrated current (charge) to a known integrated current (charge) to determine the analyte concentration, wherein the counter electrode comprises a conductor; a sheath disposed about the conductor; an electrolyte disposed within the sheath; and a porous element disposed on the sheath, the porous element providing signal communication between the electrolyte and the analyte.

DETAILED DESCRIPTION

Figure 1:
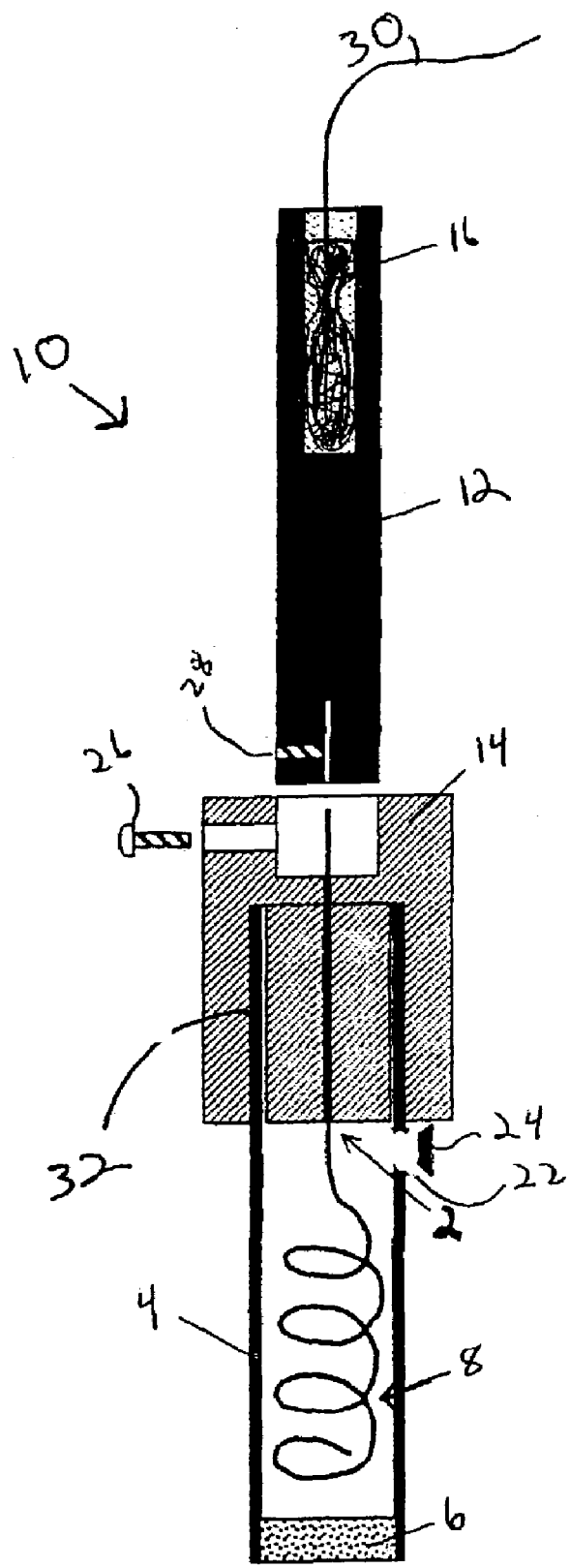
FIG. 1 is a cross sectional view of an embodiment of a counter electrode with a wire conductor.

A counter electrode capable of sustained use in an electroplating bath, and in particular, that resists becoming coated or otherwise obstructed by materials present in the electroplating composition, is obtainable by controlling the amount of physical contact between the conducting element of the counter electrode and the electroplating composition. Sequestering the conducting element, while at the same time maintaining signal communication between the conductor and the analyte solution, allows fast, accurate, and economical analysis of the bath constituents.

Turning now to the Figures and in particular FIG. 1, a counter electrode referred to generally as 10 includes a conducting element 2 (hereinafter "conductor") disposed within a sheath 4. Sheath 4 further comprises porous element 6. Also within sheath 4 is an electrolyte 8 that facilitates signal communication between conductor 2 and an analyte in the electroplating composition (not shown), Conductor 2 is electrically conductive and is preferably substantially unreactive in the electroplating bath used. Preferably, conductor 2 is a conductive metal or metal alloy, for example platinum, copper, gold, or an alloy comprising at least one of the foregoing metals. Generally, platinum or copper is preferred.

Figure 2:
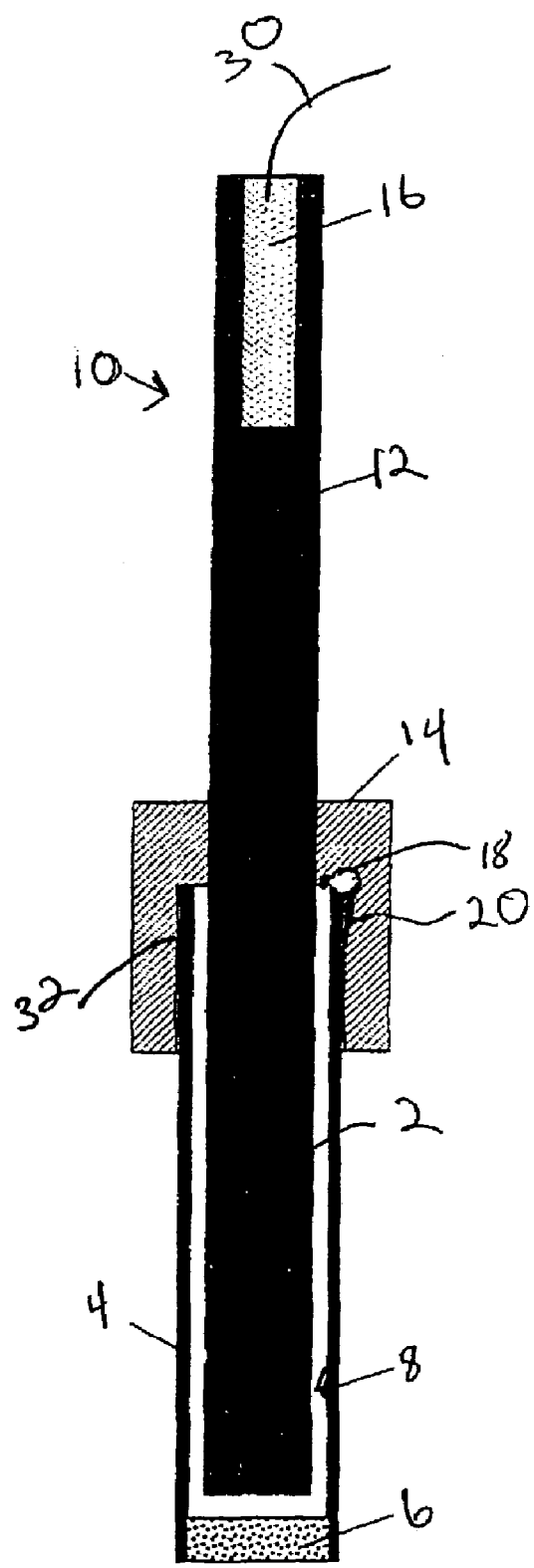
FIG. 2 is a cross sectional view of an alterative embodiment of a counter electrode with a rod conductor.

The two embodiments depicted in FIGS. 1 and 2 show conductor 2 as a wire, and as a rod, respectively. A cross-section of the conductor may include any number of geometric shapes such as, for example, a circle, a square, rectangle, and/or any combination of shapes. The conductor may also include a plurality of conductive elements, all in electrical communication with one another, for example a mesh or screen. A variety of shapes and materials are thus within the scope of the present invention.

When the conductor is a single wire, it is preferably an inert metal such as, for example, platinum having a diameter of 0.5 to 1.0 mm. The length and diameter (and thus surface area) of the wire electrode immersed in the electrolyte is preferably selected so as to be greater than or equal to the surface area of the working electrode, which is typically a disk of approximately 0.125 to 0.2 square centimeters.

In one manner of constructing the counter electrode, the wire is preferably connected to an external circuit through a handle 12 capable of providing an electrical connection to the circuit through attachment of an external lead 30. Handle 12 is dimensioned to fit within a cap 14 such that conductor 2 is in electrical communication with at least a portion of handle 12. Both handle 12 and conductor 2 are preferably secured to each other, and within cap 14, using a set screw 26 threadingly received in a hole disposed within handle 12, and arranged to provide a secure contact between handle 12 and conductor 4 as shown in FIG. 1. FIG. 1 also depicts a lead receptacle 16 to which external electrical connection 30 can be attached by, for example, inserting a "banana plug" therein.

When conductor 2 is in the form of a rod it is preferably a solid copper rod having a diameter capable of being disposed within sheath 4 and of a length such that it extends through cap 14 to serve as a handle 12. Use of a copper rod for conductor 2 also allows for direct connection of external lead 30 via lead receptacle 16. Other configurations and materials may be used, for example a hollow rod or a conductive carbon rod (especially "glassy carbon" rod), Cap 14 is non-conductive and preferably formed from a polymeric resin that is inert in the electroplating bath. Preferred materials for cap 14 include fluorocarbon resins such as polytetrafluoroethylene (commercially available under the trade name TEFLON, from DuPont de Nemours Co.). A channel 32 disposed within cap 14 is preferably dimensioned to receive sheath 4, and more preferably to provide an interference fit on one or both sides of sheath 4. In addition, or instead of an interference fit, fasteners including compression washers, O-rings, threaded members and the like may be used to secure sheath 4 within cap 14. Also, the inside surface 18 of channel 32 preferably contains notch 20 to allow for air displacement when inserting the conductor and/or electrolyte into the sheath.

Sheath 4 is formed from a non-electrically conductive material that is non-reactive in the electroplating bath. Preferred materials include glass and/or polymeric resins, including thermoplastic and thermoset resins such as polytetrafluoroethylene. Sheath 4 may also be equipped with a fill hole 22 with a sealing cover 24 to facilitate electrolyte addition, air displacement, and disassembly for cleaning.

In one embodiment, porous element 6 functions to restrict fluid flow between the electroplating composition and electrolyte 8, while still allowing for signal communication between conductor 2 and the electroplating composition. Porous element 6 is disposed so as to provide signal communication between the electrolyte and the analyte. As shown in FIGS. 1 and 4 for example, porous element 6 is conveniently disposed at an open end of sheath 4. Porous element 6 may also be disposed along a side of sheath 4.

Preferably, porous element 6 comprises fritted glass, more preferably porous high silica glass (commercially available under the trade name Vycor, from Corning Inc.). Also preferably, porous element 6 has an average pore size of 0.1 to 50 microns. Within this range, the average pore size is preferably greater than or equal to 1 microns, and more preferably greater than or equal to 2 microns. Also within this range, the average pore size is preferably less than or equal to 20 microns, and more preferably less than or equal to 10 microns on average.

In another embodiment, porous element 6 provides signal communication between the electrolyte and the analyte in the absence of direct fluid communication between the conductor 12 and the remainder of the electroplating composition. For example, porous element 6 may be a polymeric membrane responsive to, and/or selectively permeable to a particular analyte, while being essentially impermeable to ally one of the remaining components of the electroplating constituents.

Electrolyte 8 is compatible with the electroplating composition, and conducts the analytical signal from the analyte solution. The analyte solution may be the electroplating composition itself in the working bath or removed therefrom. The analyte solution may be treated (i.e., diluted) before analysis. Suitable electrolytes for transmitting the analytical signal are electrically conductive and non-reactive. Electrolytes may be in the form of liquids, gels and other semi-solid materials, and combinations comprising at least one of the foregoing. Electrolytes are typically aqueous salt solutions having a pH near or equal to the bath being analyzed. For example, in an acidic copper-electroplating bath, an aqueous copper sulfate/sulfuric acid electrolyte or sulfuric acid alone can be used to provide a high degree of signal communication between conductor 2 and the analyte via porous element 6.

Preferably, the amount of diffusion of the electroplating composition across the porous element is prevented or minimized. In one embodiment, the level of the electrolyte within sheath 4 is adjusted to substantially correspond to the level of the electroplating composition outside the counter electrode. In doing so, diffusion of organic components into sheath 4 is typically slowed enough to allow analyses over a period of several hours or more with a high level of reproducibility (i.e., less than or equal to 3% absolute error between actual and measured concentrations). At completion of analyses, sheath 4 is removed and both it and the electrode are cleaned in a suitable solvent, typically de-ionized water.

In another aspect, an electrochemical cell for analyzing an electroplating composition comprises a working electrode, a reference electrode, and a counter electrode in signal communication with an analyte solution from the electroplating composition, wherein the counter electrode comprises a conductor; a sheath disposed about the conductor; an electrolyte disposed within the sheath; and a porous element on the sheath, the porous element providing signal communication between the electrolyte and an analyte.

To determine the concentration of the analyte in the electroplating composition, the reference electrode, counter electrode 10, and the working electrode are immersed in the analyte solution. As described, for example, in U.S. Pat. No. 4,132,605, a voltammetric sweep cycle is applied to the working electrode. Current representative of the analyte concentration of the electroplating composition is drawn by the voltammetric sweep cycle and measured. The analyte concentration may then be determined by comparing the measured integrated current (charge) to a known integrated current (charge) value, for example, that obtained from a calibration curve.

While the above description is directed to the counter electrode, it is to be understood that the same principles may also be used in connection with the working and reference electrodes. All patents cited herein are incorporated by reference in their entirety.

EXAMPLES

A counter electrode in accordance with the invention was constructed as follows. The sheath was constructed by cutting a standard fritted glass tube (Ace glass, type 7209) with a diamond saw. The sheath was attached to the copper electrode with a polytetrafluoroethylene (TEFLON) cap machined to the following dimensions: 0.75 inch outside diameter×0.75 inches outside height, 0.471 inches inside diameter×0.50 inches inner height (tube), and 0.312 inches inside diameter×0.25 inches inner height (copper rod). These dimensions provided a secure fit to both the glass tube and the copper electrode, and also allowed the complete unit to be installed and removed from the analyzers (Models QL-10 and QP-4000, available from ECI Technologies, East Rutherford, N.J.) instruments with ease.

The inside surface of the cap was notched with a triangular file to allow for air displacement when inserting the copper rod into the sheath. A three-component electroplating composition was prepared containing 5.50 milliliters per liter (ml/L) of a reaction product of an amine and epichlorohydrin as a leveler component, commercially available from Shipley Company, Marlborough, Mass. This was diluted to 10% with a support solution containing 20 ml/L of a commercially availably brightener (A-2001, available from Shipley) and 40 ml/L of an ethyleneoxide ("EO")/propyleneoxide ("PO") block copolymer having a molecular weight of approximately 2500 in an electrolyte containing 35 g/L copper as copper sulfate, 45 g/L sulfuric acid and 45 ppm chloride ion. Accordingly the analyte solution contained 0.55 ml/L of the leveler component. This solution was analyzed on the ECI QL-IO-CVS instrument using a ratiometric response curve method. The response curve was obtained prior to the bath measurements by analyzing (titrating) aliquots of the leveler into the support solution.

For each sample bath measurement (Runs 1–6 of Table 1) the initial stripping peak area portion of the integrated stripping current-use (stripping charge) profile without leveler [Ar(0)], was measured followed by the bath sample. The integrated current under the stripping peak is measured in milliCoulombs (mC) of charge, and is proportional to the amount of material deposited on the working electrode during the reduction portion of the cyclic voltammetric stripping (CVS) cycle. The total amount of charge under the stripping peak is also proportional to the amount of material deposited, and may also be used for the same determination. The software then reported ratiometric result [Ar/Ar(0)] for the analyte solution and scales by the inverse of the dilution factor to give the original sample concentration. These results are illustrated in Table 1.

TABLE 1

| Run # | Temperature (° C.) | Ar(O) (mC) | Concentration (ml/L) | Error (%) |
|---|---|---|---|---|
| 1 | 21.5 | 11.05 | 5.63 | 2.30 |
| 2 | 21.4 | 11.08 | 5.58 | 1.40 |
| 3 | 21.5 | 11.25 | 5.58 | 1.40 |
| 4 | 21.5 | 11.45 | 5.42 | 1.50 |
| 5 | 21.5 | 11.54 | 5.56 | 1.00 |
| 6 | 21.9 | 11.79 | 5.52 | 0.50 |

The reproducibility and accuracy were found to be within 2.3%, a result that is 10-fold lower than obtained with analyses obtained in accordance with a prior art copper rod counter electrode in direct contact with the analyte solution. Accordingly, this level of precision allows for accurate control and dosing of acid copper electroplating baths that contain a leveler component.

What is claimed is:

1. An electrochemical cell for analyzing an analyte solution from electroplating composition comprising:
    a working electrode;
    a reference electrode; and
    a counter electrode in operable communication with the working and reference electrodes, wherein the counter electrode is in signal communication with the analyte solution, and wherein the counter electrode comprises:
    a conductor; a sheath disposed about the conductor and removably attached to a cap, the cap being non-electrically conductive; a handle dimensioned to fit within the cap and the conductor being in electrical communication with at least a portion of the handle; an electrolyte disposed within the sheath; and a porous element on the sheath, the porous element providing signal communication between the electrolyte and an analyte.

2. The electrochemical cell of claim 1, wherein the conductor comprises conductive carbon, platinum, copper, gold, or alloys comprising at least one of the foregoing metals.

3. The electrochemical cell of claim 1, wherein the conductor has a diameter of 0.5 to 1.0 mm.

4. The electrochemical cell of claim 1, wherein the porous element has an average pore size of 0.1 to 50 microns.

5. The electrochemical cell of claim 1, wherein said porous element comprises glass.

6. The electrochemical cell of claim 1, wherein the electrolyte is in the form of a liquid, gel or other semi-solid material.

7. The electrochemical cell of claim 1, wherein the conductor has a surface area equal to or greater than a surface area of the working electrode.

8. The electrochemical cell of claim 1 wherein the conductor is connected to an external circuit through the handle.

9. A method of determining an analyte concentration in an electroplating composition comprising:
   contacting the electrochemical cell of claim 1 with an electroplating composition comprising
   an analyte;
   applying a voltammetric sweep cycle to the working electrode;
   measuring a current utilized during a portion of the voltammetric sweep cycle representative of the analyte concentration; and
   determining the analyte concentration by comparing the measured integrated current (charge) to a predetermined value.

10. The method of claim 9, wherein the electroplating composition is an acid copper bath comprising a suppressor, a leveler, and a brightener.

* * * * *